United States Patent

Wessol et al.

[11] Patent Number: 5,995,864
[45] Date of Patent: Nov. 30, 1999

[54] DOSE FACTOR ENTRY AND DISPLAY TOOL FOR BNCT RADIOTHERAPY

[75] Inventors: Daniel E. Wessol, Bozeman, Mont.; Floyd J. Wheeler, Idaho Falls, Id.; Jeremy L. Cook, Greeley, Colo.

[73] Assignee: Lockheed Martin Idaho Technologies Company, Idaho Falls, Id.

[21] Appl. No.: 08/933,652

[22] Filed: Sep. 19, 1997

[51] Int. Cl.$^6$ ........................................ A61B 6/00
[52] U.S. Cl. .................................. 600/436; 128/922
[58] Field of Search .................................. 600/300, 407, 600/436; 128/898, 922; 345/9, 113

[56] References Cited

U.S. PATENT DOCUMENTS

| | | |
|---|---|---|
| 3,987,281 | 10/1976 | Hodes . |
| 5,341,292 | 8/1994 | Zamenhof . |
| 5,630,786 | 5/1997 | Griffin et al. . |
| 5,647,663 | 7/1997 | Holmes . |
| 5,800,353 | 9/1998 | McLaurin, Jr. . |
| 5,803,914 | 9/1998 | Ryals et al. . |

*Primary Examiner*—Marvin M. Lateef
*Assistant Examiner*—Shawna J. Shaw
*Attorney, Agent, or Firm*—Thorpe North & Western

[57] ABSTRACT

A system for use in Boron Neutron Capture Therapy (BNCT) radiotherapy planning where a biological distribution is calculated using a combination of conversion factors and a previously calculated physical distribution. Conversion factors are presented in a graphical spreadsheet so that a planner can easily view and modify the conversion factors. For radiotherapy in multi-component modalities, such as Fast-Neutron and BNCT, it is necessary to combine each conversion factor component to form an effective dose which is used in radiotherapy planning and evaluation. The Dose Factor Entry and Display System is designed to facilitate planner entry of appropriate conversion factors in a straightforward manner for each component. The effective isodose is then immediately computed and displayed over the appropriate background (e.g. digitized image).

16 Claims, 6 Drawing Sheets

| Dose Name | Factor | Concentration | Reference Value |
|---|---|---|---|
| Boron | 3.800000 | 15.000000 | 0.440496 |
| Gamma | 1.000000 | 1.000000 | 0.124600 |
| Nitrogen | 3.200000 | 1.840000 | 0.041824 |
| Fast | 3.200000 | 10.570000 | 0.036600 |
| total | | | 0.646600 |
| Set to Default | | Apply | Dismiss |

Fig. 2

DOSE FACTOR ENTRY AND DISPLAY TOOL FOR BNCT RADIOTHERAPY

CONTRACTUAL ORIGIN OF THE INVENTION

The United States has rights in this invention pursuant to Contract No. DE-AC07-94ID13223 between the U.S. Department of Energy and Lockheed Martin Idaho Technologies Company.

BACKGROUND

1. Field of the Invention

This invention relates to radiotherapy planning for Boron Neutron Capture Therapy (BNCT). More specifically, the present invention relates to a method for improving the simulation and display of BNCT isodoses superimposed upon the anatomical features of a patient that are to receive BNCT treatment.

2. Background Art

Application of neutrons for radiotherapy of cancer has been a subject of considerable clinical and research interest since the discovery of the neutron by Chadwick in 1932. Fast neutron radiotherapy was first used by Robert Stone in the Lawrence Berkeley Laboratory in 1938. This technology has evolved over the years to the point where it is now a very viable method for treating inoperable salivary gland tumors. On the basis of recent research data such technology also is emerging as a promising alternative for treatment for prostate cancer, some lung tumors, and certain other malignancies as well.

Neutron capture therapy (NCT), a somewhat different form of neutron-based therapy, was proposed in the mid 1930s and, despite some notable failures in early U.S. trials, has attracted a great deal of renewed research interest lately. This interest is due to significant improvements in radiobiological knowledge.

The basic physical processes involved in fast neutron therapy and neutron capture therapy differ in several respects. In fast neutron therapy, neutrons having relatively high energy (approximately 30–50 MeV) are generated by a suitable neutron source and used directly for irradiation of the treatment volume, just as is done with standard photon (x-ray) therapy. In neutron capture therapy, a neutron capture agent is injected into the patient and is selectively taken into the malignant tissue. The administration of a pharmaceutical containing the neutron capture agent is preferably accomplished by direct administration into the bloodstream of the patient. At an appropriate time after administration of the neutron capture agent, the treatment volume (i.e., the anatomical structure to be treated) is exposed to a field of thermal neutrons produced by application of an external neutron beam. Because boron-10 is commonly used as the capture agent, the technology has come to be known as boron neutron capture therapy, or BNCT.

The thermal neutrons interact with the boron-10, which has a very high capture cross-section in the thermal energy range. Ideally, the boron-10 is present only in the malignant cells so that boron-neutron interactions will occur only in malignant cells. Each boron-neutron interaction produces an alpha particle and a lithium ion. These highly-energetic charged particles deposit their energy within a geometric volume that is comparable to the size of the malignant cell. Thus, boron-neutron interaction provides a high probability of cell inactivation by direct DNA damage.

Because boron is ideally taken up only in the malignant cells, the NCT process offers the possibility of highly selective destruction of malignant tissue while causing minimal damage to the normal tissue disposed adjacent to the tumor. When boron-10 is taken up in the malignant cells only, the separation between normal and malignant tissue occurs on a cellular-level basis—thereby providing considerable accuracy. In addition, the neutron sources used for NCT are, themselves, designed to produce a minimal level of damage to normal tissue which has not received the neutron capture agent.

When BNCT is administered as a primary therapy, an epithermal-neutron beam (neutrons having energies in the range of 1 eV to 10 keV) is used to produce the required thermal neutron flux at depth. This is because these somewhat higher-energy neutrons will penetrate deeper into the irradiation volume before thermalizing. Although the neutrons penetrate deeper, they are still not of sufficient energy to inflict unacceptable damage to intervening normal tissue.

A third form of neutron therapy is also a subject of current research interest. The third form of neutron therapy is basically a hybrid that combines the features of fast neutron therapy and NCT. In this type of radiotherapy, a neutron capture agent is introduced into a patient—preferably into the malignant tissue only. This treatment is prior to the administration of standard fast neutron therapy. Because a small fraction of the neutrons in fast neutron therapy will be thermalized in the irradiation volume, it is possible to obtain a small incremental absorbed dose from the neutron capture interactions that result. Thus, based on current radiobiological research, improved tumor control appears to be likely when using the augmentation concept.

One significant problem with the various neutron therapy systems is that they are usually located only at major research centers because they are physically complex, bulky, expensive to acquire and require high-level operating staffs to maintain. In general these systems are not well suited for wide-spread, practical, clinical deployment.

This disadvantage is compounded by the fact that in BNCT and other neutron therapy systems detailed planning calculations are necessary to optimize the treatment for each individual patient. Careful planning permits the delivery of the highest possible therapeutic radiation dose to the target tissue while maintaining the surrounding healthy tissue at or below tolerance. However, extensive planning can limit the number of patients which can be properly treated using neutron therapy equipment. Thus, in recent years significant efforts have been made to develop modern computational methods and software for use in BNCT treatment planning.

One such treatment planning system for BNCT has been developed by the New England Medical Center Hospitals. This system is described in U.S. Pat. No. 5,341,292 (Zamenhof), entitled Monte Carlo Based Treatment Planning for Neutron Capture Therapy. The Zamenhof system displays a patient image superimposed with isodose contour lines. To obtain a patient image superimposed with isodose contour lines, the system must process both a physical distribution and a biological distribution. Processing both the physical and biological distributions each time a planner desires to view isodose contours on a patient image is inefficient and time consuming.

In addition, the Zamenhof system uses an undesirable method to eliminate unwanted isodose contours. Isodose contours appear everywhere that they are computed to appear—even in areas of the display that do not have a patient image. The isodose contours that appear outside the patient image are undesirable. To get rid of these contour lines, the Zamenhof method sets computed isodose values outside the patient image to zero. Zamenhof, Col. 2, lines 2–4. Setting the computed isodose values to zero in the air regions outside the patient image causes the isodose curves to have unrealistic dropouts near the margins of the patient image. These dropouts are sharp and cause a general distortion throughout the isodose curves.

Other treatment planning systems consider the isodose contours to consist of one component and present the contours on top of a medical image or graphical, visual representation of anatomical features. Although these systems increase the speed of treatment planning, they are not as accurate as desired.

Thus, there is a need for a method for treatment planning that provides for isodose contour line displays superimposed over a patient image, while eliminating the contour lines in areas not of concern to the planner. Such a system should be easy to use and enable more efficient treatment planning.

OBJECTS AND SUMMARY OF THE INVENTION

It is an object of the present Invention to provide a system for displaying an accurate model of isodoses used in BNCT and related types of radiotherapy.

It is another object of the present invention to provide such a system which enables a graphic display of an image of a desired anatomical feature of a patient with isodose contours superimposed thereon to reflect radiotherapy treatment.

It is, yet another object of the present invention to enable the planner to select what portion of the anatomical feature and the surrounding area is displayed.

The present invention involves a method and a system, wherein the method involves processing signals to generate a visual display of a desired anatomical feature. Isodose contour lines representative of the radiotherapy are superimposed over the anatomical feature displayed so as to indicate the effect of the neutron therapy on the patient. A raster image is then superimposed on the anatomical feature of the patient and isodose contour lines to selectively mask the contour lines in areas other than the desired anatomical feature so that isodose contour lines that are not wanted will not appear. What determines which isodose contour lines are undesired and will not appear can be controlled by the planner to thereby facilitate planning of the radiotherapy.

In accordance with another aspect of the present invention, the system includes a processor, typically a computer, connected to a display. The processor is programmed to process information supplied by the planner to develop a graphical representation of the anatomical feature undergoing treatment, to develop a visual representation of the neutron propagation (contour lines) and to develop a raster image which selectively masks the undesired contour lines.

The present invention provides a convenient way for the planner to rescale the isodose curves, accounting for tissue-specific biological factors and concentration. Primarily, the invention will reduce the amount of clinical staff time spent developing a specific treatment plan. This, in turn, can increase the quality of the plan and patient throughput. An increased patient throughput allows for more efficient usage of expensive resources and thereby makes radiotherapy more cost efficient than in the past. Other advantages will become apparent from the detailed description and the claims.

In accordance with one aspect of the invention, the steps of providing a visual representation of the anatomical feature, superimposing an isodose pattern of contour lines generated by processing of the weighting values and applying a raster image to selectively mask contour lines outside a desired area is repeated until a desired contour line pattern is viewed on the display. With the desired contour line pattern present on the screen, the operator may then quickly determine the proper radiotherapy dose.

BRIEF DESCRIPTION OF THE DRAWINGS

The above and other objects, features and advantages of the invention will become apparent from a consideration of the following detailed description presented in connection with the accompanying drawings in which:

FIG. 2 is an illustration of a graphical display of the dose entry and display tool of the preferred embodiment of the present invention, where the tool shows the dose components used to calculate a final conversion factor in determining a biological distribution in a patient of a planned radiotherapy.

DETAILED DESCRIPTION OF THE PREFERRED EMBODIMENTS

Figure 1:
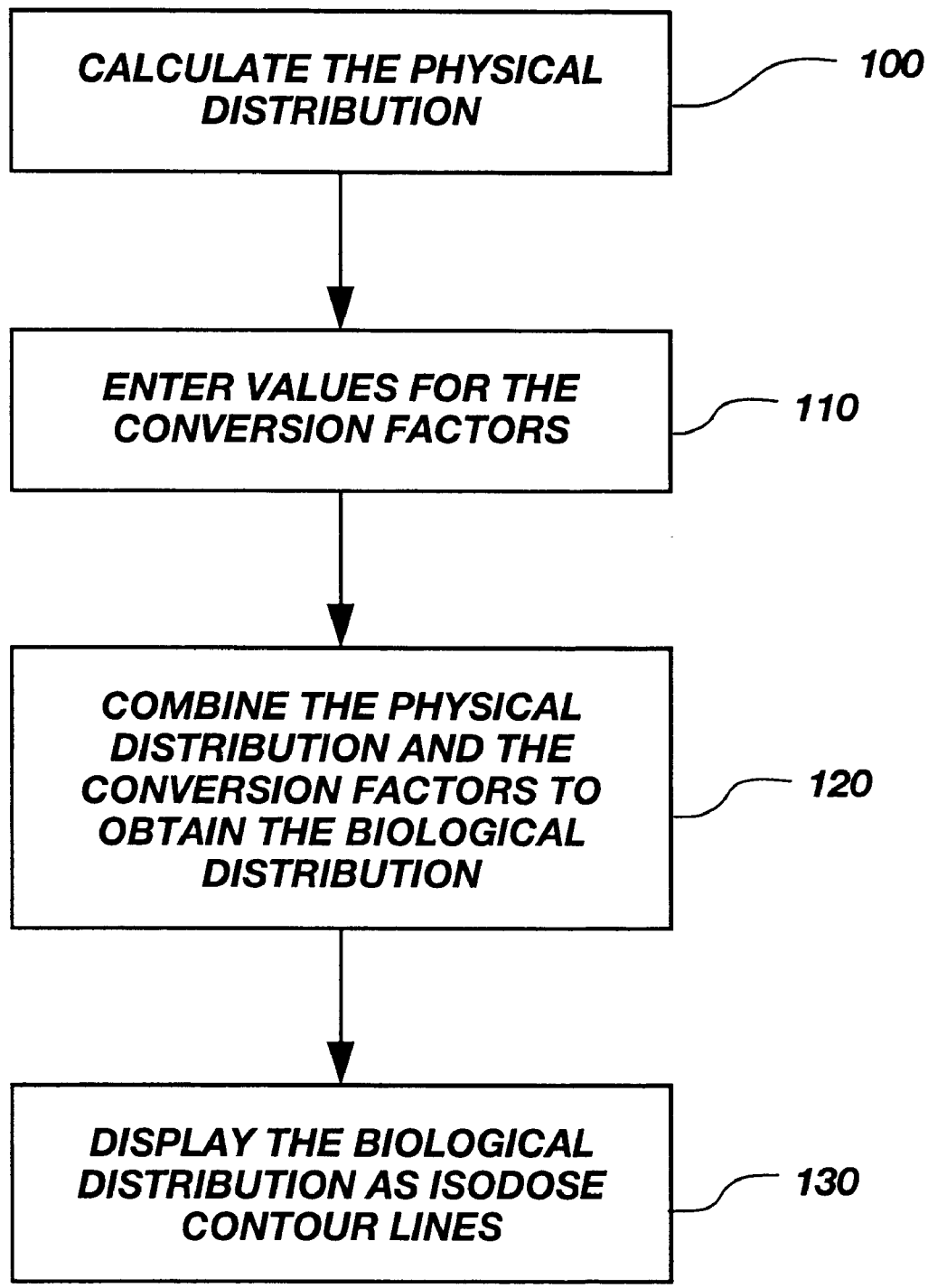
FIG. 1 is a flow chart of the method of the preferred embodiment of the present invention which explains the steps of radiotherapy planning.

Reference will now be made to the drawings in which the various elements of the present invention will be given numerical designations and in which the invention will be discussed so as to enable one skilled in the art to make and use the invention. It is to be understood that the following description is only exemplary of the principles of the present invention, and should not be viewed as narrowing the pending claims.

The method for more easily displaying an accurate model of isodose contour lines from Boron Neutron Capture Therapy (BNCT) or other related radiotherapies includes a number of steps. By following these steps, the present method results in better radiotherapy planning. Better radiotherapy planning will minimize the adverse affects of BNCT radiotherapy on a patient's normal tissues, while at the same time improving planning time and patient throughput.

A preferred embodiment of the present invention comprises a method for assisting BNCT radiotherapy planning which includes using a new planning tool to be described below. In order to understand how the new planning tool provides a method which assists in BNCT planning, it is appropriate to look at the preferred embodiment of the invention in context of existing BNCT planning.

As stated previously, two elements are combined to calculate and then display isodose contour lines. As understood by those skilled in the art, isodose contour lines are displayed superimposed upon an image of patient tissue. The displayed combination is referred to as a biological distribution. Typically, the image is a cross section of the patient's tissue which is to receive the BNCT radiotherapy, but it can also be a three dimensional image, with three dimensional isodose contour lines.

The two elements which are combined in radiotherapy planning are a physical distribution and a radiotherapy conversion factor. The physical distribution is a mathematical description of the patient's tissue which is to be subjected to BNCT radiotherapy, and is obtained typically through a lengthy computer calculation. Once calculated, the physical distribution is stored for retrieval when needed to calculate the biological distribution.

In the state of the art, a conversion factor is a reference value which is combined with the physical distribution to obtain the biological distribution. The conversion factor itself is a result which is derived from a combination of dose or weighting factors as will be explained. Consequently, the biological distribution displayed as isodose contour lines on a cross section of the patient's tissue is the predicted effect of BNCT radiotherapy based on the calculated physical distribution and the preselected conversion factor. In summary, the method is summarized as a) calculating the physical distribution, b) determining the biological distribution by combining the physical distribution and the conversion factor, and c) displaying the biological distribution as isodose contour lines superimposed upon a patient's tissue.

The conversion factor, or more accurately the factors which are used to derive the conversion factor, are the subject of much dispute among those skilled in the art. Unfortunately, BNCT radiotherapy planning is based upon a conversion factor which is typically hard wired into a calculation which is used to generate the isodose contour lines, despite the controversy about the value of the conversion factor. In other words, existing equipment for generating and displaying isodose contour lines typically comes with a predefined conversion factor. The disadvantage to this approach is that given the disagreement which exists, there is no easy method for generating isodose contour lines on a graphical display where the person conducting the BNCT radiotherapy planning believes that a different conversion factor should be used without repeating. Therefore, regardless of the fact that empirical or experimental data might suggest a different conversion factor, it is not an adjustable factor in BNCT radiotherapy planning.

The preferred embodiment of the present invention is a solution to the present inability to do more accurate BNCT radiotherapy planning by providing a method for adjusting the conversion factor. More specifically, the method is provided for adjusting numerous conversion factors which are combined together to reach a final conversion factor. The preferred embodiment of the present invention is made clear from a detailed description of the following method as also shown in FIG. 1.

The first step 100 of the method is to obtain the physical distribution, exactly as done in the prior art. Again, the physical distribution only heeds to be calculated once and stored for retrieval in later calculations. Therefore, the physical distribution might have been calculated previous to application of the remaining steps. But it is important to realize that the physical distribution is not recalculated each time new isodose contour lines are displayed.

The second step 110 of the method is to enter on a computer display the values for the conversion factors as shown in a table which is represented in FIG. 2. FIG. 2 shows all the factors which are adjustable by the planner when generating the isodose contour lines in radiotherapy planning. Consequently, the method of step two 110 defines a major point of novelty of the present invention. Unlike the hard wired conversion value used in the method of the prior art, the factors which are used to generate the conversion value of the preferred embodiment are shown as adjustable quantities. These conversion factors can be adjusted using an automated or manual method.

The automated method is to input the conversion factors from a radiation transport module. Those skilled in the art of radiotherapy planning understand the functions of the radiation transport module and the information derivable therefrom, so it is unnecessary to describe its operation in detail.

The manual method of entering conversion factors is simply to use a computer keyboard to modify the values. The values are modified by moving a cursor using any method known to those skilled in the art such as with a mouse or moving between fields by tapping on a movement key. What is important to the preferred embodiment of the present invention is that the conversion factors are adjustable. This greatly improves the ability of radiotherapy planning to become more of a useful tool which allows for disagreements in conversion factors to be visualized. Consequently, better planning is accomplished when examining a range of conversion factors. Therefore, it is important to look at what conversion factors can be adjusted.

FIG. 2 shows a table shown generally as item 8 in a spread-sheet like display of conversion factors. The first column identifies the different components 12 which are used to calculated a final conversion factor 10 to be used in calculating the isodose contour lines. Those skilled in the art will recognize the components shown in the first column, and the identities 12 do not constitute part of the present invention.

The second column is labelled "Factor" and is defined as a relative biologic effect factor 14, or compound Factor. The third column is defined as the "Concentration" factor 16. The values for the concentration factors 16 vary depending upon the component 12. The final column is defined as "Reference Value" 18.

In the present invention, the reference values 18 are determined by the planner and typically represent a maximum dose to tissue at risk. The reference values 18 have been multiplied by the relative biologic effect factors 14 and the concentration factors 16. For the Boron component, the concentration factor 16 is specified in parts per million of boron by weight which is supposed to be present in the tissue which is to receive the radiotherapy. For the Gamma component, the concentration factor 16 is not meaningful and is typically set to unity. For the nitrogen component, the concentration factor 16 is displayed as percent by weight of nitrogen in the affected tissue as a result of radiotherapy. Finally, for the Fast component, the concentration factor 16 is displayed as a percent by weight of hydrogen.

The end result of entering the relative biologic effect factors 14, and the concentration factor 16 either manually or automatically, is that the final concentration factor 10 is calculated and displayed. Advantageously, the planner then has three options 20, 22 and 24. The first option 20 is to delete all values and reset them to some predefined values 14, 16, and 18 which are stored in the system. The second option 22 is to apply the conversion factors as shown and generate the isodose contour lines on a graphical display. The third option 24 is to dismiss or leave the Dose Factor Tool.

It should be apparent from the method for generating the final conversion value 10 above that the planning tool 8 represents significant versatility in recalculating isodose contour lines by being able to rapidly modify conversion factors. Given this new tool 8, radiotherapy planners will be able to analyze a wide variety of possible and differing isodose contour lines according to various opinions as to what the correct conversion factors 14, 16 and 18 might be. Consequently, planners are able to adjust treatment in light of a range of different conversion factors 14, 16 and 18.

Continuing with the steps leading to the improved radiotherapy planning process, the third step 120 (FIG. 1) comprises using the conversion factor derived in FIG. 2 and the previously calculated physical distribution to generate the biological distribution.

Figure 3:
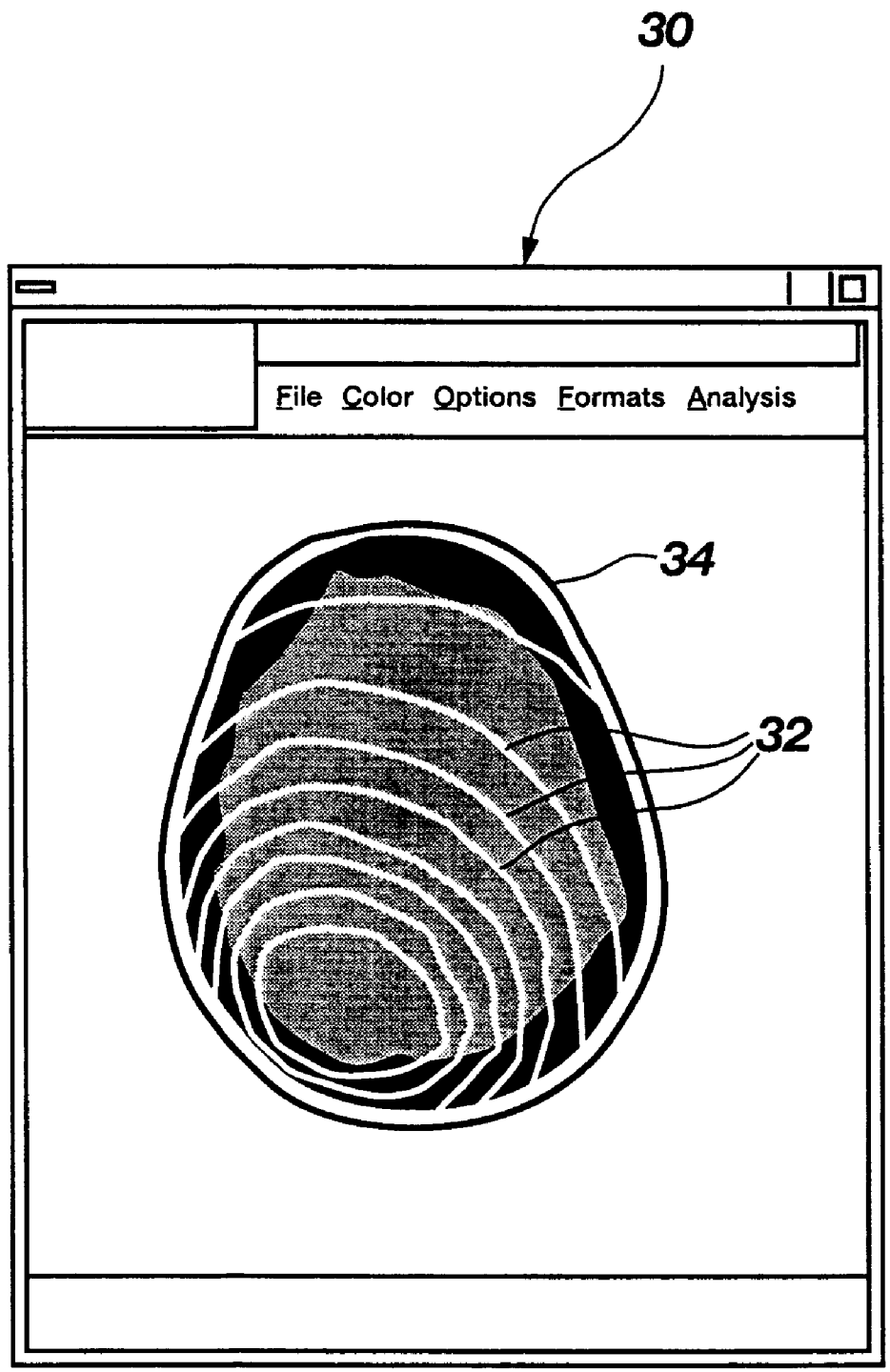
FIG. 3 is an illustration of a graphical display which shows the biological distribution represented by isodose contour lines superimposed upon an anatomical feature of the patient, wherein the biological distribution is a physical distribution combined with the conversion factors, where the isodose contour lines are shown using nominal conversion factor values.

The fourth step 130 (FIG. 1) is then comprised of displaying a graphical representation 30 of the biological distribution as shown in FIG. 3. As stated before, the biological distribution is shown as isodose contour lines 32 superimposed upon an image of the patient's tissue 34. Those skilled in the art are able to display an image of the patient's tissue 34 from an appropriate source, and is not a subject of the present invention. What is important to remember is that the isodose contour lines 32 now represent the conversion factors which are now easily modifiable in the conversion factors tool 8 shown in FIG. 2.

Figure 4:
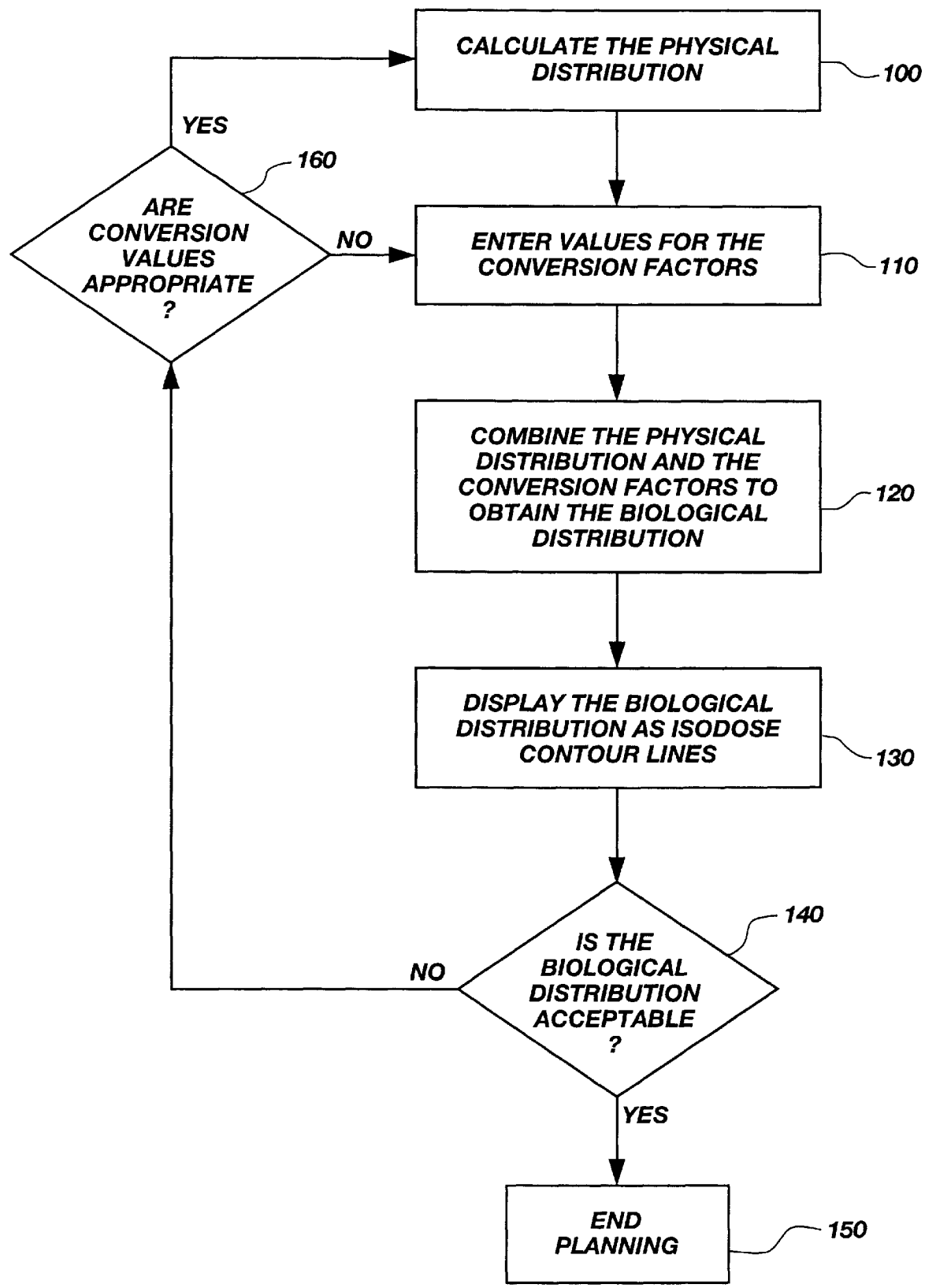
FIG. 4 is a modified flowchart of the present invention showing additional steps in an alternative embodiment

The conversion factors tool 8 shown in FIG. 2 is only one of the significant points of novelty of the present invention. FIG. 4 shows a flow chart which adds additional steps to the method of the preferred embodiment. In this alternative embodiment, after generating the image 30 shown in FIG. 3, the planner may decide in the fifth step 140 that the conversion factors 14, 16 and 18 need to be modified to obtain a more advantageous or acceptable biological distribution. The prior art has no conversion factors tool 8 as does the present invention for rapidly entering new conversion factors which are then combined with the stored physical distribution to generate the new conversion factor 10.

If the conversion factors 14, 16 and 18 are to be modified, the planner now advantageously has the ability to return to the conversion factors tool 8. However, step 160 first asks the planner to decide whether the conversion values are appropriate. If they are, the planner must recalculate the physical distribution in step 100. Otherwise, the conversion values are not appropriate, and the planner should make modifications to the conversion factors 14, 16 and 18 as in step 110. When completed, the planner then applies the new conversion factors to the physical distribution so that a new biological distribution can be displayed. However, if the planner believes that the biological distribution is accurate and requires no modification, the radiotherapy planning is complete as shown in step 150.

Figure 5:
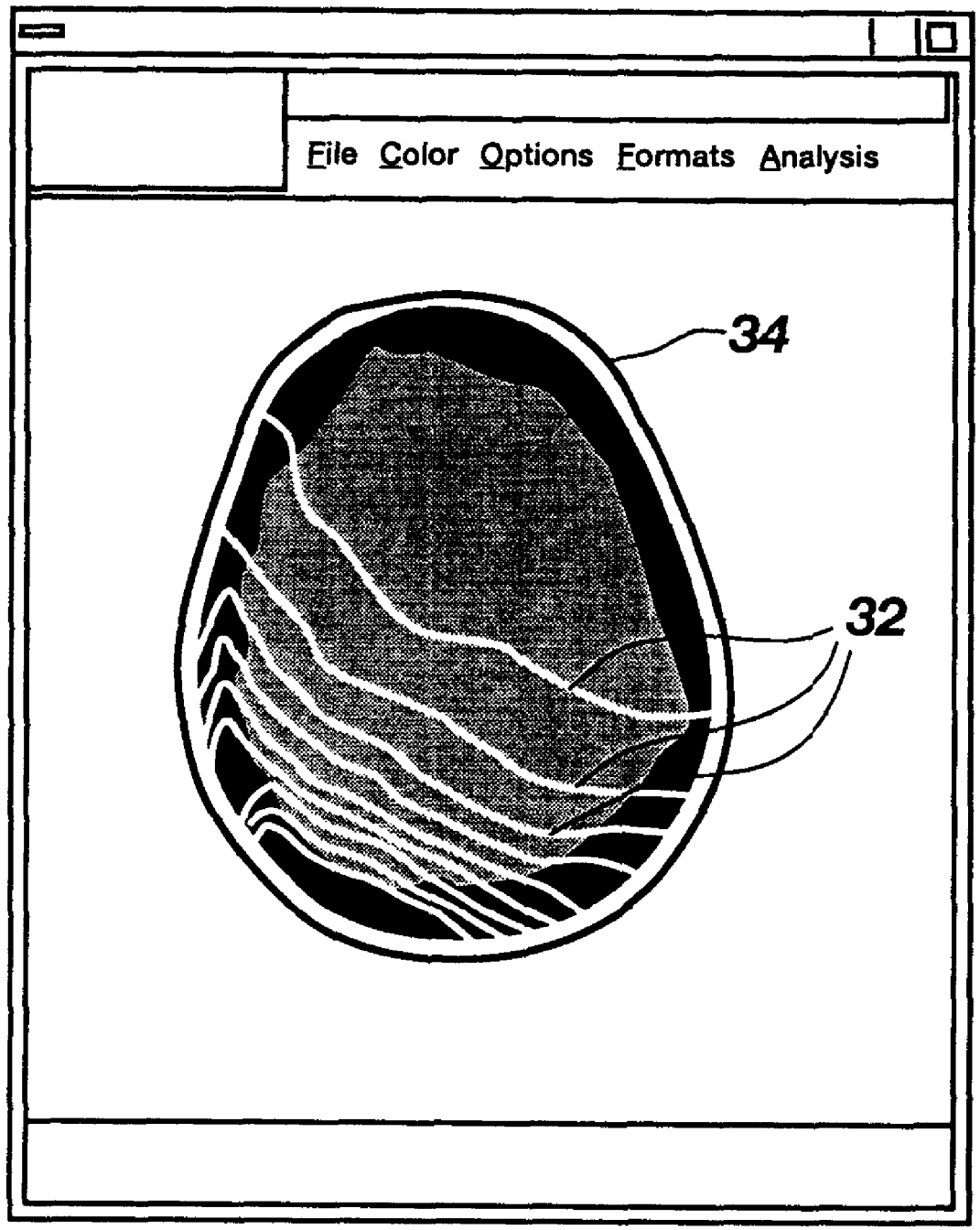
FIG. 5 is an illustration of a graphical display which shows the biological distribution represented by isodose contour lines superimposed upon the anatomical feature of the patient, wherein the biological distribution is the physical distribution combined with the conversion factors, where the isodose contour lines are shown using an extreme set of conversion factor values set to zero except for hydrogen.

As an example of a new biological distribution, a new set of conversion factors was entered into the conversion factors tool 8 in order to generate FIG. 5. FIG. 5 shows an extreme case of conversion factors 14, 16 and 18 where all concentration factors 16 are set to zero, except for the hydrogen concentration of the Fast component 12. As FIG. 5 shows, the isodose contour lines 32 are dramatically skewed as compared to the isodose contour lines of FIG. 3.

Figure 6:
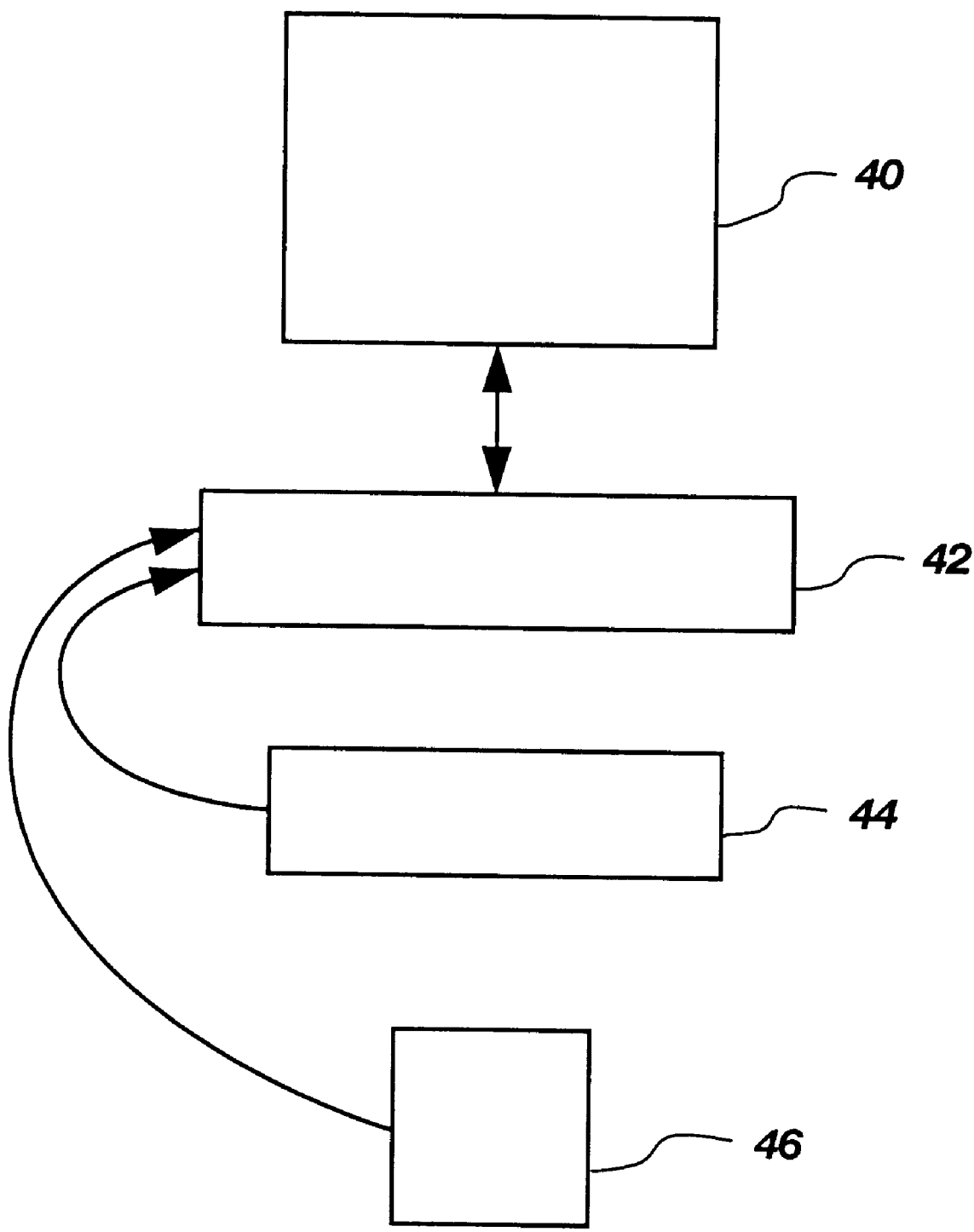
FIG. 6 is a block diagram of the apparatus of the preferred embodiment of the present invention, including a graphical display, a general purpose computer, and a keyboard or radiation transport module for entering data.

Aside from the new method of the present invention, the system for executing the steps of the preferred embodiment includes three main components shown in block diagram form in FIG. 6:

(1) a graphical display 40 for displaying the conversion factors tool 8 (FIG. 2) to enable rapid input of conversion factors, and for displaying the biological distribution as a plurality of isodose contour lines 32 (FIG. 3) superimposed over an image 30 of the patient's tissue 34;

(2) a means for carrying out the computations necessary for obtaining a physical distribution, the final conversion factor 10 (FIG. 2), and the biological distribution. This means is typically a general purpose computer 42; and (3) a means for entering the conversion factors 14, 16 and 18 (FIG. 2) to be displayed in the conversion factors tool 8 and used in the biological distribution calculations, such as a computer keyboard 44 or a radiation transport module 46.

These system components make it possible to use the conversion factors tool 8 to select the planners own set of conversion factors 14, 16 and 18 to thereby generate biological distributions displayed as isodose contour lines 32. Furthermore, they also simplify the process of then making modifications to the conversion factors by bringing up the conversion factors tool 8 on the graphical display, making the modifications, and then selecting the option to apply the new conversion factors 14, 16 and 18 to the stored physical distribution.

The conversion factors that are to be entered by the planner or the radiation transport module can be estimated or taken from a list that is prepared by someone skilled in the art.

It is to be understood that the above-described arrangements are only illustrative of the application of the principles of the present invention. Numerous modifications and alternative arrangements may be devised by those skilled in the art without departing from the spirit and scope of the present invention. The appended claims are intended to cover such modifications and arrangements.

We claim:

1. A method for radiotherapy planning for Boron Neutron Capture Therapy (BNCT), comprising the steps of:

(a) calculating a physical distribution for an anatomical feature of a patient;

(b) entering at least one selectable conversion factor from a radiation transport module using a conversion factors entry and display tool, the radiation transport module having an output electrically coupled to a computer for loading the at least one selectable conversion factor into the computer;

(c) combining the physical distribution and the at least one selectable conversion factor to generate a biological distribution within the anatomical feature; and (d) displaying the biological distribution as isodose contour lines superimposed over an image of the anatomical feature.

2. The method for radiotherapy planning as defined in claim 1 wherein the step of entering the at least one selectable conversion factor comprises the more specific step of entering the at least one selectable conversion factor at a computer keyboard.

3. The method for radiotherapy planning as defined in claim 2 wherein the step of entering selectable conversion factors includes the step of entering selectable conversion factors for at least one dose component selected from the group consisting of dose components comprising boron, gamma, nitrogen and fast.

4. The method for radiotherapy planning as defined in claim 3 wherein the step of entering selectable conversion factors includes the step of entering at least one reference value which represents the maximum dose of the anatomical feature at risk.

5. The method for radiotherapy planning as defined in claim 3 wherein the step of entering selectable conversion factors includes the step of entering at least one relative biologic effect factor.

6. The method for radiotherapy planning as defined in claim 3 wherein the step of entering selectable conversion factors includes the step of entering at least one concentration factor.

7. The method for radiotherapy planning as defined in claim 6 wherein the step of entering at least one concentration factor includes the specific step of specifying boron in parts per million by weight which is supposed to be present in the anatomical feature receiving the radiotherapy.

8. The method for radiotherapy planning as defined in claim 6 wherein the step of entering at least one concentration factor includes the specific step of specifying gamma as unity.

9. The method for radiotherapy planning as defined in claim 6 wherein the step of entering at least one concentration factor includes the specific step of specifying nitrogen as percent by weight in the anatomical feature as a result of radiotherapy.

10. The method for radiotherapy planning as defined in claim 6 wherein the step of entering at least one concentration factor includes the specific step of specifying fast as a percent by weight of hydrogen in the tissue of interest.

11. The method for radiotherapy planning as defined in claim 1 wherein the step of entering at least one selectable conversion factor comprises the more specific step of generating a final reference value which is the sum of the reference values.

12. The method for radiotherapy planning as defined in claim 1 wherein the step of calculating a physical distribution comprises the more specific step of saving the physical distribution for the anatomical feature.

13. The method for radiotherapy planning as defined in claim 12 wherein the method comprises the more specific steps of:
   (a) determining whether the biological distribution is acceptable; and
   (b) if not acceptable, recalling the saved physical distribution and repeating steps (b), (c) and (d) of claim 1 until the biological distribution is acceptable, or if acceptable, terminating the method.

14. The method for radiotherapy planning as defined in claim 1 wherein the method comprises the more specific step of planning Fast Neutron Capture Therapy.

15. The method for radiotherapy planning as defined in claim 14 wherein the method comprises the more specific step of planning a hybrid combination of BNCT and Fast Neutron Capture Therapy.

16. A system for radiotherapy planning for treatment of an anatomical feature, said system comprising:
   a first graphical display for showing a conversion factors entry and display tool for entering at least one conversion factor;
   a radiation transport module having an output electrically coupled to a computer for loading the at least one conversion factor into the computer;
   a means for calculating a physical distribution for the anatomical feature of the patient, and for calculating a biological distribution from the calculated physical distribution and all of the conversion factors; and
   a second graphical display for showing the biological distribution as isodose contour lines superimposed over the anatomical feature.

* * * * *